United States Patent [19]
Wood et al.

[11] Patent Number: 5,260,066
[45] Date of Patent: Nov. 9, 1993

[54] CRYOGEL BANDAGE CONTAINING THERAPEUTIC AGENT

[75] Inventors: Louis L. Wood, Rockville; Gary J. Calton, Elkridge, both of Md.

[73] Assignee: SRCHEM Incorporated, Elkridge, Md.

[21] Appl. No.: 821,627

[22] Filed: Jan. 16, 1992

[51] Int. Cl.$^5$ .............................................. A61L 15/16
[52] U.S. Cl. ................................... 424/447; 424/443; 424/445; 424/486
[58] Field of Search ................. 424/447, 443, 445, 486

[56] References Cited

U.S. PATENT DOCUMENTS

| | | | |
|---|---|---|---|
| 3,875,302 | 4/1975 | Ione | 426/1 |
| 3,949,073 | 4/1976 | Daniels et al. | 424/177 |
| 4,221,778 | 9/1980 | Raghunathan | 424/31 |
| 4,265,233 | 5/1981 | Sugitachi | 128/156 |
| 4,472,542 | 9/1984 | Nambu | 523/309 |
| 4,492,685 | 1/1985 | Keith | 424/28 |
| 4,552,138 | 11/1985 | Hofeditz | 128/156 |
| 4,664,857 | 5/1987 | Nambu | 264/28 |
| 4,692,462 | 9/1987 | Banerjee | 514/449 |
| 4,781,926 | 11/1988 | Hyon | 424/486 |
| 4,808,353 | 2/1989 | Nambu et al. | 264/28 |
| 4,847,077 | 7/1989 | Raghunathan | 424/79 |
| 4,931,279 | 6/1990 | Bawa | 424/427 |
| 4,996,047 | 2/1991 | Kelleher et al. | 424/79 |
| 5,012,503 | 4/1991 | Nambu et al. | 378/64 |
| 5,082,663 | 1/1992 | Konishi | 424/445 |

FOREIGN PATENT DOCUMENTS 1-299216 12/1989 Japan.
1-299228 12/1989 Japan.

OTHER PUBLICATIONS

K. Morimoto et al., Evaluation of polyvinyl alcohol hydrogel Drug Development and Industrial Pharmacy, 16(1), 13-29 (1990).
K. Morimoto et al., Design of a polyvinyl alcohol hydrogel J. Pharm. Pharmacol. 1990, 42: 720-722.
K. Morimoto et al., Evaluation of polyvinyl alcohol hydrogel Pharmaceutical Research, vol. 6, No. 4, 1989, pp. 338-341.
K. Morimoto et al. Design of a poly(vinyl alcohol) hydrogel Chem. Pharm. Bull. 37, 2491-2495, 1989.
Peppas, N. A. and E. W. Merrill, Development of semi-crystalline J. Biomed. Mater. Res. vol. 11, pp. 423-434 (1977).
A. Takamura et al. Drug release from freeze-thaw poly(vinyl alcohol) gel. Yakugaku Zasshi 107(3) 233-237 (1987).
K. Tamura et al. A new hydrogel and its medical application vol. XXXII Trans. Am. Soc Artif. Intern. Organs 1968 pp. 605-608.
N. Peppas et al. Reinforced uncrosslinked poly(vinyl alcohol) Journal of Controlled Release 16 (1991) 305-310.
H. Ogawara et al. Manufacture of poultices on stretchable Chemical Abstracts vol. 112, 1990, 112:223319t.
A. Nakagawa et al. Hydrogel-containing poultices. Chemical Abstracts vol. 113, 1990. 113: 198046n.
D. Murray et al. Hydrogel-forming wound dressing or skin Chemical Abstracts vol. 113, 1990. 113: 120867m.
F. Nakahara et al. Spherical water-containing poly(vinyl alcohol) Chemical Abstracts vol. 114, 1991 114: 25265a.
F. Feng Study on the state of water in cryo-hydrogel. Chemical Abstracts vol. 113, 1990. 113: 98578u.
M. Roreger et al. Flexible, hydrophilic, insoluble, swellable Chemical Abstracts vol. 113, 1990. 113: 158748m.

(List continued on next page.)

Primary Examiner—Thurman K. Page
Assistant Examiner—D. Gabrielle Phelan
Attorney, Agent, or Firm—William S. Ramsey

[57] ABSTRACT

A controlled-release bandage containing therapeutic agents in a poly(vinyl alcohol) cryogel is disclosed. The bandage may include particulate absorbants such as ion exchange resins and hydrophobic particles to further insure controlled and constant release of therapeutic agents. The bandage may also include plasticizing agents to provide softness in the event of drying the bandage.

8 Claims, No Drawings

OTHER PUBLICATIONS

K. Ichimura et al. Artificial intraocular lens containing Chemical Abstracts vol. 113, 1990. 113: 120860d.

K. Sakurai et al. Manufacture of skin substitute with poly Chemical Abstracts vol. 113, 1990. 113: 65314b.

V. I. Lozinskii et al. Some thermomechanical properties of Chemical Abstracts vol. 112, 1990. 112: 57261w.

V. I. Lozinskii et al. Characteristic features of the freezing Chemical Abstracts. vol. 112, 1990. 112: 37116z.

S. Hayashi et al. Preparation of oriented hydrogel membranes Chemical Abstracts. vol. 112, 1990. 112: 57695r.

B. Gander et al. Structural analysis of poly(vinyl alcohol) Chemical Abstracts vol. 112, 1990. 112: 42412x.

S. Hyon et al. Preparation of poly(vinyl alcohol) hydrogels Chemical Abstracts. vol. 112, 1990. 112: 99763a.

M. Shigemitsu. Manufacture of poultice or topical patch with Chemical Abstracts vol. 111, 1989. 111: 239584r.

J. Gen et al. Poly(vinyl alcohol) hydrogels, their manufacture Chemical Abstracts vol. 114, 1991. 114: 44209b.

A. Sorokin et al. Change in the crystallinity of cross-linked Chemical Abstracts vol. 113, 1990. 113: 120756z.

S. Hyon. Poly(vinyl alcohol) hydrogel with intermolecular Chemical Abstracts 114, 1991. 114: 144304x.

M. Nambu. Rubber-like poly(vinyl alcohol) gel. Chemical Abstracts vol. 113, 1990. 113: 192272m.

T. Shiomi. Preparation and application of poly(vinyl alcohol Chemical Abstracts vol. 112, 1990. 112: 140670z.

M. Sunami et al. Haloperidol transdermal films. Chemical Abstracts vol. 112, 1990. 112: 240484k.

M. Sunami et al. Transdermal films for drug preparations. Chemical Abstracts vol. 112, 1990. 112: 240485m.

A. Takamura et al. Drug release from freeze-thaw poly(vinyl Chemical Abstracts vol. 106, 1987. 106: 219473x.

K. Morimoto et al. Design of a poly(vinyl alcohol) hydrogel Chemical Abstracts vol. 114, 1991. 114: 30084v.

M. Kuraiki et al. Application of transparent poly(vinyl Chemical Abstracts vol. 112, 1990. 112: 100221x.

Y. Mizutani et al. Manufacture of contact lenses with poly Chemical Abstracts vol. 111, 1989. 111: 45330r.

F. Urushizaki et al. Swelling and mechanical properties of Chemical Abstracts vol. 113, 1990. 113: 46197z.

N. Voitko et al. Poly(vinyl alcohol) films for medical ap Chemical Abstracts vol. 114, 1991. 114: 214358u.

K. Mihori et al. Evaluation of polyvinyl alcohol hydrogel Graef's Arch Clin Exp Ophthalmol (1990) 228: 533–537.

F. Urushizaki et al. Swelling and mechanical properties of Journal of Pharmaceutics, 58 (1990) 135–142.

CRYOGEL BANDAGE CONTAINING THERAPEUTIC AGENT

FIELD OF THE INVENTION

This invention relates to bandages which are used to administer therapeutic agents.

BACKGROUND OF THE INVENTION

Cryogels are solid elastomers containing over 80% water which are produced when solutions of higher molecular weight poly(vinyl alcohol) (PVA) of high degree of hydrolysis are subjected to repeated freeze-thaw cycles. Such cryogels are tough, slippery, elastomeric, resilient, insoluble in water below 50° C., and nontoxic.

The fact that cryogels may be produced without the use of cross-linking agents or other adjuvants is a desirable feature emphasized in a review of the scientific literature on such gels (N. A. Peppas and S. R. Stauffer. Reinforced uncrosslinked poly(vinyl alcohol) gels produced by cyclic freezing-thawing processes: a short review. Journal of Controlled Release, 16, 305-310, 1991).

Transdermal films of PVA containing drugs such as corticosteroids, inflammation inhibitors, sedatives, tranquilizers, antihypertensives, diuretics, antibiotics, anesthetics, and vitamins have been disclosed (M. Sunamiu, et al, Transdermal films for drug preparations. Chemical Abstracts 112:240485m, 1990). These films used PVA of 500-2400 degree of polymerization (molecular weight of about 22,000-105,000 daltons) and were used to administer pharmaceuticals through the skin.

The anti-inflammatory indomethacin has been incorporated into cryogels. Its release was found to be in direct proportion to the square of time. PVA cryogels cross-linked with glutaraldehyde were shown to release indomethacin with zero order kinetics (A. Takamura, M. Arai, F. Ishii. Drug release from freeze-thaw poly(vinyl alcohol) gel. Yakugaku Zasshi, 107, 233-237, 1987).

PVA hydrogels have been used as rectal suppositories for controlled release for beta-blockers. Straight line release of the drugs superior to that of other suppositories was observed (K. Morimoto, S. Fukanoki, K. Morisaka, S. Hyon and Y. Ikada. Design of a poly(vinyl alcohol) hydrogel as a controlled-release vehicle for rectal administration of dl-propranolol hydrochloride and atenolol. Chem. Pharm. Bull. 37, 2491-2495, 1989).

The inclusion of phospholipids in the PVA hydrogels was shown to slow the release of propranolol (K. Morimoto, S. Fukanoki, Y. Hatakeyama, A. Nagayasu, K. Morisaka, S. Hyon. Design of a poly(vinyl alcohol) hydrogel containing phospholipid as controlled-release vehicle for rectal administration of (+/−)-propranolol hydrochloride. J. Pharm. Pharmacol, 42, 720-722, 1990).

Hydrogels containing indomethacin, however, were inferior to conventional suppositories in their effect on dog plasma levels (K. Morimoto, A. Nagayasu, S. Fukanoki, K. Morisaka, S. Hyon and Y. Ikada. Evaluation of poly(vinyl alcohol) hydrogels as a sustained-release vehicle for rectal administration of indomethacin. Pharm. Research, 6, 338-341, 1989).

PVA hydrogels containing bunitrolol-HCl gave straight line release as the square of time over 60% of the total release time (K. Morimoto, A. Nagayasu, S. Fukanoki, K. Morisaka, S. Hyon and Y. Ikada. Evaluation of poly(vinyl alcohol) hydrogel as sustained-release vehicle for transdermal system of bunitrolol-HCl. Drug Devel. Ind. Phar., 16, 13-29, 1990).

The manufacture of a poultice or topical patch for transdermal delivery by wrapping a film which may contain a polyhydric alcohol, starch, hyaluronic acid or propylene glycol alginate with a PVA sheet has been disclosed (M. Shigemitsu, Jpn KTK 01 16,718, Jan. 20, 1989).

The use of PVA hydrogel as a soft contact lens material has been reported (M. Kita, Y. Ogura, Y. Honda, S Hyon, W. Cha and Y. Ikada. Evaluation of polyvinyl alcohol hydrogel as a soft contact lens material. Graefe's Arch. Clin. Exp. Ophthal. 228, 533-537, 1990).

Controlled-release systems for oral administration of therapeutic agents are described in U.S. Pat. No. 4,221,778 to Raghunathan, issued Sep. 9, 1980 in which a preparation of a drug resin complex is coated with an impregnating agent in order to provide the desired controlled release the drug.

Controlled-release systems for oral administration of therapeutic agents are described in U.S. Pat. No. 4,847,077 to Raghunathan, issued Jul. 11, 1989 in which a preparation of a drug resin complex is coated with glycerin and then coated with a water-permeable diffusion barrier in order to provide the desired controlled release of the drug.

Controlled-release systems for oral administration of therapeutic agents are described in U.S. Pat. No. 4,996,047 to Kelleher et al, issued Feb. 26, 1991 in which a preparation of a drug resin complex having a drug content above 38% by weight is coated with a water-permeable diffusion barrier.

Although these poly(vinyl alcohol) cryogel materials have been used to accomplish transdermal delivery, the prior art has not disclosed compositions of poly(vinyl alcohol) and methods of their preparation for bandages which effectively release therapeutic agents directly to a wound, trauma or surgical site. The use of ion exchange resins incapsulated in various coatings for oral administration of therapeutic agents has been described, however, the prior art has not disclosed the use of ion exchange resins incapsulated in poly(vinyl alcohol) cryogels for use in bandages which effectively release therapeutic agents directly to a wound, trauma or surgical site. The prior art has also not disclosed the use of ion exchange-drug complexes enclosed in poly(vinyl alcohol) cryogels for the transdermal delivery of therapeutic agents or for use in oral pharmaceutical preparations for administration of drugs in the gastrointestinal tract.

SUMMARY OF THE INVENTION

Bandages comprising cryogel and therapeutic agents are used to provide a protective covering and to provide a controlled and uniform administration of therapeutic agents to sites of trauma such as wound, thermal or chemical burns, ulcers, lesions or surgical sites.

Cryogel bandages may include, in addition to the therapeutic agent and the cryogel components, absorbent materials such as ion exchange resins or particles having hydrophobic properties, which absorb the therapeutic agent and release it in an uniform and controlled manner.

The object of this invention is to provide means for delivering effective dosages of therapeutic agents to sites of trauma such as wounds, thermal or chemical burns, ulcers, lesions or surgical sites.

Another object of this invention is to maintain relatively constant dosages of therapeutic agents to sites of trauma such as wounds, thermal or chemical burns, ulcers, lesions or surgical sites.

Another object of this invention is to prevent wide variation in the concentration of therapeutic agents to sites of trauma such as wounds, thermal or chemical burns, ulcers, lesions or surgical sites.

Another object of this invention is to provide a protective, comforting cover to sites of trauma such as wounds, thermal or chemical burns, ulcers, lesions or surgical sites.

Another object of this invention is to provide a sterile infection resisting bandage for protecting sites of trauma.

Another object of this invention is to provide a means of delivering effective dosages of therapeutic agents transdermally.

Another object of the present invention is to provide an oral pharmaceutical composition of a drug-resin complex coated with a flexible coating that is insoluble in gastrointestinal fluids thereby providing a coating which is independent of the quantity of drug complexed, the size of the ion exchange resin, or the ion exchange capacity of the resin, resulting in a controllable sustained release of the drug under conditions encountered in the gastrointestinal tract.

A final object is to provide a controlled-release bandage constructed of inexpensive materials.

DETAILED DESCRIPTION OF THE EMBODIMENTS

In this disclosure, the term "%" means % by weight. "Cryogel" means a hydrogel containing poly(vinyl alcohol) (PVA) which has been treated by one or more freeze-thaw cycles. The term "degree of hydrolysis" means the percentage of acetate groups which have been hydrolyzed to alcohol groups in the preparation of the PVA. The term "mobile phase" means the liquid phase used for elution of components in the HPLC methods. The term "bandage" means a PVA cryogel containing a therapeutic agent and is distinguished from a poultice on which the therapeutic agent is spread.

The proper polymeric matrix for this PVA cryogel bandage invention is selected from commercially available PVA's having molecular weights >50,000 (preferably <90,000 and usually <200,000 and having a degree of hydrolysis >90% (preferably 98 to 100%). A preferred embodiment used PVA of molecular weight 110,000–186,000 daltons. Aqueous solutions of the desired PVA polymers are prepared by stirring the desired mixture of PVA and water at temperatures >60° C. (preferably 80° C. to 100° C.) until a homogeneous solution is formed (usually 1 to 2 hours). The concentration of PVA in water can be as low as 1% or as high as 20%. However, cryogels made of <5% PVA in water were found to undergo appreciable syneresis (complete separation of appreciable amounts of water from the bulk of the retaining cryogel) during their preparation. Solutions of >15% PVA in water were difficult to manipulate. This is because the required high molecular weight PVA (>50,000) formed very viscous to semi-solid solutions at 25° C. at concentrations in water exceeding 15%. The preferred range of PVA concentrations is about 7.5% to 15%.

It was desirable to steam autoclave PVA solutions at 100° to 120° C. under pressure (to prevent loss of water) for 20 to 60 minutes to insure the PVA solutions were sterile.

After this sterilization, it was convenient to add whatever other sterile solid or liquid components (antibiotics, growth factors, therapeutic agents, etc. discussed in a following section) needed in the final bandage device of this invention.

The PVA solutions in water plus components were fabricated into the desired solid elastomeric PVA cryogel configurations of the invention as follows. These solutions (or solutions plus suspensions) in the amounts of 0.01 to 500 g (usually 0.05 to 50 g) were poured into the cavity of a desirably shaped mold. The mold should be made of any non-interactive, dimensionally stable materials such as stainless steel, polypropylene, higher polyolefins, polyacrylates, polycarbonates, polysulfones and the like which may have coverings of polymer films.

To generate the desired PVA cryogel compositions the mold and its contents were then subjected to cycles of freezing (0° to −80° C., usually −10° to −25° C.) and thawing (+1° to +30° C., usually +20° to +25° C.). The number of freeze/thaw cycles can be as low as two or as high as time will allow. The strength of the PVA cryogel elastomer increased with each successive freeze/thaw cycle. Usually we found three to five freeze/thaw cycles were sufficient. The smaller increments of strength gained above five cycles are usually not significant. The durations of each freeze and thaw period can be as little as 2 minutes to as long as 16 hours. We observe that 20 to 30 minutes is all that is normally required. The resultant PVA cryogel shapes are tough, slippery, translucent, elastomeric shapes having 85 to 95% water content.

Of major importance to this PVA cryogel device invention are the specific components added to the PVA cryogel for controlled delivery. These components and their proposed function are listed in Table I. It is contemplated that one or more of the components selected from those listed in Table I will be an integral part of the device at appropriate therapeutic levels.

Table I

Therapeutic Agent Additives to the PVA Cryogel Bandages for Controlled Release

Antibiotics including those:
  inhibiting cell wall formation: bacampicillin, bacitracin, cephalosporins(including cephalothin, cefazolin, cephapirin, cephradine, cephalexin, cefadroxil, cefaclor, cefamandole cefuroxime, cefonicid, ceforanide, cefoxitin, cefotaxime, ceftizoxime, cefoperazone, ceftazidime, ceftriaxone, moxalactam, imipenem/cilastatin), cycloserine, penicillins (including penicillin G, penicillin G benzathine, cloxacillin, dicloxacillin, methicillin, nafacillin, oxacillin, penicillin V, ampicillin, amoxicillin, bacampicillin, syclacillin, carbenicillin, tircarcillin, mezlocillin, piperacillin, azlocillin, amdinocillin, penicillins combined with clavulanic acid), vancomycin, other β-lactam antibiotics;
  disrupting DNA metabolism: actinomycin D, doxorubicin, mitomycin C, novobiocin, plicamycin, rifampin, bleomycin;
  inhibiting protein biosynthesis: amikacin, chloramphenicol, clindamycin, erythromycin, oleandomycin, gentamicin, kanamycin, lincomycin, neomycin, netilmicin, paromomycin, spectinomycin, streptomycin, tetracyclines (including tetracycline, oxytetracycline, demeclocycline, doxycycline, methacycline, minocycline,), tobramycin, troleandomycin;

altering cellular membrane functions: amphotericin B, colistin, nystatin, polymyxin, griseofulvin;

quinolones including: nalidixic acid, pipemidic acid, cinoxacin, norfloxacin, ciprofloxacin, pefloxacin, fleroxacin, enoxacin, ofloxacin, tosufloxacin, lomefloxacin, stereoisomers of the quinolones;

Antimicrobials including: sulfacetamide, sulfisoxazole diolamine, salts of monovalent and divalent cations, inorganic and organic silver salts, inorganic and organic zinc salts;

Antipathogenic polypeptides including: cecropionins, mangainins;

antibacterial and antifungal agents including: iodine, povidone iodine, boric acid, sodium borate, oxydale, potassium permanganate, ethanol, isopropanol, formalin, cresol, dimazole, siccanin, phenyliodoundecynoate, hexachlorophene, resorcin, benzethonin chloride, sodium lauryl sulfate, mercuric chloride, meclocycline, mercurochrome, chlorhexidine gluconate, alkylpolyaminoethylglycine hydrochloride, benzalkonium chloride, nitrofurazone, nystatin, acesulfamin, clotrimazole, sulfamethizole, tolnaftate, pentamycin, amphotericin B, pyrrolnitrin, undecylenic acid, miconazole, trichomycin, variotin, haloprogin, and dimazole;

Antiviral Agents including: idoxuridine, trifluridine, vidarabine, DDCl, acyclovir, gancyclovir, pyrimethamine, trisulfapyrimidine, flucytosine, AZT;

Steroidal Anti-inflammatory including: cortisone, hydrocortisone, prednisolone, prednisone, dexamethasone, fluocinolone, fluorinated-corticoids Nonsteroidal Anti-inflammatory Drugs including: diclofenac, ibuprofen, naproxen, ketoprofen, S-ketoprofen;

Anti-cancer Drugs including: aclacinomycin, retinoic acid, methotrexate, doxorubicin, IL-1$\alpha$, IL-2, IL-2$\beta$, IL-3, IL-4, bleomycin, mitomycin, taxol, cis-platinum, bisantrene, CCNU, activated cytoxan, DTIC, HMM, melphalan, mithromycin, procarbazine, VM25, VP16, tamoxifen, plicamycin, 5-fluorouracil, daunorubicin, mitomycin C, tegafur, carmofur, pipobroman, peplomycin;

Antihistamines including: naphazoline, pheniramine, cromolyn, homochlorocyclizine hydrochloride, diphenhydramine hydrochloride, chlorpheniramine, diphenylimidazole, glycyrrhetic acid, tranilast, and ketotifen;

Anti-clotting Agents including: TPA, urokinase, streptokinase, pro-urokinase;

Anti-tissue Damage Agents including: superoxide dismutase;

Immune Modulators including: lymphokines, monokines, interferon $\alpha$, $\beta$, $\tau$-1b, $\alpha$-n3, $\alpha$-2b, $\alpha$-2b; Growth Regulators including: IL-2, tumor necrosis factor, epithelial growth factor, somatrem, fibronectin, GM-CSF, CSF, platelet derived growth factor, somatotropin, rG-CSF, epidermal growth factor, IGF-1;

Monoclonal and Polyclonal Antibodies including those active against: venoms, toxins, tumor necrosis factor, bacteria;

Hormones including epinephrine, levarterenol, thyroxine, thyroglobulin, oxytocin, vasopressin, ACTH, somatropin, thyrotropin, insulin, parathyrin, calcitonin;

Immunosuppressives including: cyclosporin,

Thrombolytic Agents including: tissue plasminogen activator, streptokinase, pro-urokinase, urokinase, Vitamins including: vitamins A, B and its subvitamins, C, D, E, F, G, G, J, K, N, P, PP, T, U and their subspecies;

Amino Acids including: arginine, histidine, proline, lysine, methionine, alanine, phenylalanine, aspartic acid, glutamic acid, glutamine, threonine, tryptophan, glycine, isoleucine, leucine;

Prostaglandins including: $E_1$, $E_2$, $F_{2\alpha}$, $I_2$;

Enzymes including: pepsin, pancreatin, rennin, papain, trypsin, pancrelipase, chymopapain, bromelain, chymotrypsin, streptokinase, urokinase, tissue plasminogen activator, fibrinolysin, desoxyribonuclease, sutilains, collagenase, asparaginase, heparin;

Buffers and Salts including: NaCl, cations including: $Na^+$, $K^+$, $Ca^{++}$, $Mg^{++}$, $Zn^{++}$, $NH_4^+$ triethanolamine, anions including: phosphate, sulfate, chloride, citrate, ascorbate, acetate, borate, carbonate ions;

Preservatives including: benzalkonium chloride, Na or K bisulfite, Na or K thiosulfate, parabans;

Vasodilators including: nitroglycerin, 1,2,3-propanetriolmononitrate, 1,2,3-propanetriolnitrate and their ester derivatives, isosorbide dinitrate, isosorbide-5-mononitrate, pentaerythritol tetranitrate, papaverine hydrochloride, hepronicate, molsidomine, nicomol, simfibrate, diltiazem hydrochloride, cinnarizine, dipyridamole, trapidil, trimetazidine hydrochloride, carbocromene, prenylamine lactate, dilazep dihydrochloride;

Antiarrhythmic agents including: pindolol, disopyramide, bupranolol hydrochloride, trichlormethiazide, furosemide, prazosin hydrochloride, metoprolol tartrate, carteolol hydrochloride, oxprenolol hydrochloride, and propranolol hydrochloride;

Cardiotonics including: metildigoxin, caffeine, dopamine hydrochloride, dobutamine hydrochloride, octopamine hydrochloride, diprophylline, ubidecarenon, digitalis, digoxin;

Antihypertensives including clonidine, nifedipine, nicardipine, verapamil;

Local Anesthetics including: lidocaine, benzocaine, ethyl aminobenzoate, procaine hydrochloride, dibucaine, procaine;

Hypotensive diuretics including: mefruside, penflutizide, bumetamide, hydrothiazide, bentroflumethiazide, reserpine;

Hypnotics and sedatives including: methaqualone, glutethimide, flurazepam, bromovalerylurea, flurazepam hydrochloride, haloxazolam, traizolam, phenobarbital, chloral hydrate, nimetazepam, estazolam;

Central nervous system agents including: levodopa, fluphenazine, flutazolam, phenobarbital, methylphenobarbital, thioridazine, diazepam, benzbromarone, clocapraminehydrochloride, clotiazepam, chlorpromazine, haloperidol, lithium carbonate;

Antitubercular agents including: sulfadimethoxine, sulfisoxazole, sulfisomidine, ethambutor hydrochloride, isoniazide, calcium paraaminosalicylate;

Post-cerebral embolism agents including: nicardipine hydrochloride, cinepazide maleate, pentoxifylline, ifenprodil tartrate;

Antiulcer agents including: aceglutamide aluminum, cetraxate hydrochloride, pirenzepine hydrochloride, cimetidine, L-glutamine, gefarnate;

and any stereoisomer of these compounds, and the pharmaceutically acceptable salts of these compounds, such compound used singly or in combination of more than one compound, properly chosen.

The release of therapeutic agents from the bandage has been found to be further controllable by including insoluble particles capable of adsorbing or forming salts with the therapeutic agent in the bandage. The release of therapeutic agents from such bandages was found to be slowed and maintained at a relatively constant rate, as compared to the release of therapeutic agents from bandages not containing insoluble particles. The inclusion of insoluble particles is an important aspect of embodiments in which the characteristic therapeutic agent release kinetics are desired.

Examples of suitable insoluble particles include ion exchange beads functionalized with a strong acid, weak strong base, or weak base. Other examples of suitable insoluble particles include hydrophobic resins, silica, hydroxy apatite and aluminum oxide.

The insoluble particles or beads may be incorporated into the bandage along with the therapeutic agent before the bandage is subjected to freeze/thaw treatment. Alternatively, insoluble particles may be incorporated in the bandage in the absence of therapeutic agents. After such a bandage is formed, it may be immersed in an aqueous solution or suspension of therapeutic agent. The agent is imbibed by such a bandage and is subsequently released from the bandage in a controlled manner.

Other additives which may be optionally included in the bandage include preservatives, such as benzalkonium chloride, sodium or potassium bisulfite, sodium or potassium thiosulfate, parabens and diazolidinyl urea.

The pH and ionic strength of the bandage may be controlled as appropriate by including buffers and salts. Examples include salts such as sodium chloride; cations such as $Na^+$, $K^+$, $Ca^{++}$, $Mg^{++}$, $Zn^{++}$, $NH_4^+$, triethanolamine, and anions such as phosphate, sulfate, chloride, citrate, ascorbate, acetate, borate, and carbonate.

Other additives which serve as lubricants and plasticizers may be optionally included in the bandage. Examples of these are glycerol, propylene glycol, poly(propylene glycols), poly(ethylene glycols), propylene and ethylene oxide copolymers, hydroxypropyl methyl cellulose, poly(vinyl pyrrolidone), hydroxyethyl cellulose, carboxymethyl cellulose, hyaluronic acid, poly(vinyl alcohol), dextrans;

The PVA cryogel bandage may be supported by a woven or non-woven fabric or film support. The support may be attached to one surface of the cryogel bandage, or the support may be incorporated or cast into the body of the bandage. Suitable supports include woven fabrics of naturally occurring fibers, woven fabrics of man made fibers, non-woven fabrics of naturally occurring fibers, non-woven fabrics of man-made fibers, strands of naturally occurring fibers, strands of man-made fibers, interconnected strands of man-made fibers and interconnected strands of naturally occurring fibers, foams of polymeric materials, and naturally occurring sponges. A water and/or water vapor impermeable covering may be applied after the cryogel bandage or as a component.

The following examples illustrate embodiments of the subject invention wherein both essential and optional ingredients are combined.

EXAMPLE 1

Preparation of a Cryogel Bandage Containing Tobramycin

A solution of 20 mg tobramycin (Sigma Chem. Co.) in 200 mg of a 10% polyvinyl alcohol (110,000 molecular weight; 100% hydrolyzed) solution in water was a viscous, clear colorless liquid. A 120 mg portion of this mobile solution was placed in a stainless steel mold having a cavity 30 mil thick and 18 mm in diameter. The mold and its contents were subjected to the following freeze/thaw cycles:

(a) $-20°$ C., 10 hrs.; $25°$ C., one hour
(b) $-20°$ C., one hour; $25°$ C., one hour and
(c) $-20°$ C., one hour; $25°$ C., one hour The resultant 120 mg solid cryogel bandage was slippery, nearly transparent and had good elastomeric properties.

EXAMPLE 2

Ciprofloxacin HCl in Neutral PVA Hydrogel Bandage

A slurry was made of 11.0 mg of ciprofloxacin HCl and 200 mg 10% poly(vinyl alcohol), 110,000 molecular weight, 100% hydrolysis. Upon warming to $50°-60°$ C., a clear homogeneous solution was formed. Upon cooling to $25°$ C., the solution became a uniformly hazy white slurry. A 100 mg portion of this slurry, estimated to contain 5.5 mg of ciprofloxacin, was placed in a mold and subjected to six freeze/thaw cycles ($-20°$ C., 20–45 min/$25°$ C., 20–45 min per cycle) to give a white opaque elastomeric cryogel bandage (15 mm diameter, 0.5 mm thick).

The bandage was placed in a capped vial containing 1 ml of 0.9% NaCl in distilled water at $25°$ C. After 1 hr of gentle stirring, the aqueous phase was collected and the bandage was placed in a fresh 1 ml portion of 0.9% NaCl. This process was repeated for a total of 24 one hour periods. The following procedure for HPLC analysis of ciprofloxacin was essentially that of Darouiche, R. et al, [J. Inf Dis 162, 1124–1125 (1990)]. The conditions were a Whatman Partisil 50D5-3 (C8) column with a mobile phase of 25 ml 0.5M $Bu_4NHPO_4$ made up to 2.5 L with distilled water, pH adjusted to 2.34 with 85% $H_3PO_4$, which was added to 278 ml HPLC grade acetonitrile, filtered through a $0.2\mu$ membrane and degassed. The flow rate was 1.5 ml/min at $25°$ C. with a 500 $\mu l$ injection loop with detection at 280 nm. Under these conditions ciprofloxacin eluted as a single peak at 9 min. HPLC analysis of the 24 aqueous fractions gave the elution profile shown in Table 2. The data in Table 2 showed that 74% of the initial charge of ciprofloxacin was released in the first 4 hrs and the release of ciprofloxacin in the subsequent 5 to 24 hrs was remarkably constant. This was thought to be due to the gradual release of ciprofloxacin trapped in the cryogel matrix.

TABLE 2

| Time, Hr | $\mu g$ cipro/ml | Time, Hr | $\mu g$ cipro/ml | Time, Hr | $\mu g$ cipro/ml |
|---|---|---|---|---|---|
| 1 | 3200 | 9 | 92 | 17 | |
| 2 | 640 | 10 | 92 | 18 | |
| 3 | 144 | 11 | 92 | 19 | 67 |
| 4 | 100 | 12 | 92 | 20 | 64 |
| 5 | 96 | 13 | 76 | 21 | 60 |
| 6 | 92 | 14 | 78 | 22 | 50 |
| 7 | 96 | 15 | 46 | 23 | 50 |
| 8 | 96 | 16 | 76 | 24 | 45 |

EXAMPLE 3

Ciprofloxacin Salt with Styrene Sulfonic Acid Resin Bead in a PVA Cryogel Bandage A solution of 10 mg ciprofloxacin HCl in 20 ml of distilled water was neutralized to pH 7.0 with 30 μl of 1N NaOH. The resultant clear solution was gently stirred with 100 mg of wet styrene sulfonic acid ion exchange resin beads in the $H^+$ form (Bio-Rad AG50W-X4, 35-75μ diameter, washed 2 times with methanol, 2 times with 1N HCl and two times with distilled water) for six hours at 25° C. At this point HPLC analysis showed no ciprofloxacin present in the solution. All ciprofloxacin had been absorbed by the beads.

The beads were drained free of the aqueous phase and 300 mg of a 10% poly(vinyl alcohol), 110,000 mol. wt., 100% hydrolyzed, solution in distilled water was added. A 100 mg portion of the resultant slurry was cast into a bandage by a series of 6 freeze/thaw cycles as described in Example 2. This bandage was estimated to contain 2.5 mg of ciprofloxacin.

This bandage containing the ciprofloxacin/styrene sulfonic acid bead salt was subjected to hourly extractions with 1 ml portions of 0.9% NaCl at 25° C. and the extracts were analyzed for ciprofloxacin content by HPLC as described in Example 2. The results were as shown in Table 3. The data in Table 3 showed that only about 4% of the initial charge of ciprofloxacin was released in the first 4 hours and that the release of ciprofloxacin over the subsequent 20 hrs was remarkably level between 23 and 65 μg/ml.

TABLE 3

| Time, Hr | μg cipro/ml | Time, Hr | μg cipro/ml | Time, Hr | μg cipro/ml |
|---|---|---|---|---|---|
| 1 | 27 | 9 | 60 | 17 | 31 |
| 2 | 31 | 10 | 65 | 18 | 46 |
| 3 | 29 | 11 | 60 | 19 | 35 |
| 4 | 25 | 12 | 60 | 20 | 31 |
| 5 | 24 | 13 | 50 | 21 | 31 |
| 6 | 20 | 14 | 60 | 22 | 31 |
| 7 | 20 | 15 | 46 | 23 | 26 |
| 8 | 28 | 16 | 45 | 24 | 23 |

EXAMPLE 4

Higher Concentrations of Ciprofloxacin Salt with Styrene Sulfonic Acid Resin Bead in a PVA Cryogel Bandage A solution of 50 mg ciprofloxacin HCl in 20 ml of distilled water was neutralized to pH 7.0 with 150 μl of 1N NaOH. The resultant hazy slurry was gently stirred with 100 mg of wet styrene sulfonic acid ion exchange resin beads in the $H^+$ form (Bio-Rad AG50W-X4, 35-75μ diameter, washed 2 times with methanol, 2 times with 1N HCl and two times with distilled water) for sixteen hours at 25° C. to give a clear colorless aqueous solution over the resin beads. At this point HPLC analysis showed 80 μg/ml of ciprofloxacin present in the solution. Thus the beads were estimated to contain 48.4 mg of ciprofloxacin.

The beads were drained free of the aqueous phase and 300 mg of a 10% poly(vinyl alcohol), 110,000 mol. wt., 100% hydrolyzed, solution in distilled water was added. A 100 mg portion of the resultant slurry was cast into a bandage by a series of 6 freeze/thaw cycles as described in Example 2. This bandage was estimated to contain 12.1 mg of ciprofloxacin.

This bandage containing the ciprofloxacin/styrene sulfonic acid bead salt was subjected to hourly extractions with 1 ml portions of 0.9% NaCl at 25° C. and the extracts were analyzed for ciprofloxacin content by HPLC as described in Example 2. The results obtained are shown in Table 4. The data in Table 4 showed that less than 3% of the initial charge of ciprofloxacin was released in the first 4 hours, the release of ciprofloxacin over the subsequent 20 hrs was remarkably constant and that the pH of the extracts was 7.0.

TABLE 4

| Time, Hr | μg cipro/ml | Time, Hr | μg cipro/ml | Time, Hr | μg cipro/ml |
|---|---|---|---|---|---|
| 1 | 290 | 9 | 160 | 17 | 170 |
| 2 | 260 | 10 | 150 | 18 | 150 |
| 3 | 250 | 11 | 160 | 19 | 170 |
| 4 | 240 | 12 | 150 | 20 | 170 |
| 5 | 200 | 13 | 150 | 21 | 160 |
| 6 | 190 | 14 | 170 | 22 | 160 |
| 7 | 160 | 15 | 180 | 23 | 150 |
| 8 | 160 | 16 | 180 | 24 | 145 |

EXAMPLE 5

A Cryogel/Resin Bead Bandage wherein the Cryogel/Resin Bead $H^+$ Form Was First Formed and then Imbibed with Ciprofloxacin to Form a Salt A slurry of 100 mg of wet styrene sulfonic acid ion exchange resin beads in the $H^+$ form (Bio-Rad AG50W-X4, 35-75μ diameter, washed 2 times with methanol, 2 times with 1N HCl and two times with distilled water) were drained free of the aqueous phase and 300 mg of a 10% poly(vinyl alcohol), 110,000 mol. wt., 100% hydrolyzed, solution in distilled water added. A 100 mg portion of the resultant slurry was cast into a bandage by a series of 6 freeze/thaw cycles as described in Example 2. The bandage was then immersed in a mixture of 30 mg ciprofloxacin HCl in 20 ml of distilled water and neutralized to pH 7.0 with 90 μl of 1N NaOH. After gentle stirring for 24 hrs at 25° C., a clear solution over the bandage device was obtained. At this point HPLC analysis showed 2.4 mg of ciprofloxacin present in the solution. Thus the bandage was estimated to contain 27.6 mg of ciprofloxacin.

This bandage containing the ciprofloxacin/styrene sulfonic acid bead salt was subjected to hourly extractions with 1 ml portions of 0.9% NaCl at 25° C. and the extracts were analyzed for ciprofloxacin content by HPLC as described in Example 2. The results of this experiment are shown in Table 5. Table 5 showed that less than 6% of the initial charge of ciprofloxacin was released in the first 4 hours, the release of ciprofloxacin over the subsequent 20 hrs was fairly constant between 140 and 272 μg/ml and that the pH of the extracts was 7.0.

TABLE 5

| Time, Hr | μg cipro/ml | Time, Hr | μg cipro/ml | Time, Hr | μg cipro/ml |
|---|---|---|---|---|---|
| 1 | 330 | 9 | 260 | 17 | 176 |
| 2 | 320 | 10 | 248 | 18 | 168 |
| 3 | 320 | 11 | 232 | 19 | 160 |
| 4 | 320 | 12 | 232 | 20 | 170 |
| 5 | 312 | 13 | 208 | 21 | 140 |
| 6 | 248 | 14 | 208 | 22 | 140 |
| 7 | 256 | 15 | 208 | 23 | 140 |

TABLE 5-continued

| Time, Hr | μg cipro/ml | Time, Hr | μg cipro/ml | Time, Hr | μg cipro/ml |
|---|---|---|---|---|---|
| 8 | 272 | 16 | 208 | 24 | 150 |

EXAMPLE 6

A Bandage of Styrene Sulfonic Acid Beads in a PVA/Glutaraldehyde Crosslinked Matrix which Was then Imbibed with Ciprofloxacin to Form a Salt A slurry of 1.25 mg of wet styrene sulfonic acid ion exchange resin beads in the H+ form (Bio-Rad AG50W-X4, 35–75μ diameter, washed 2 times with methanol, 2 times with 1N HCl and two times with distilled water) in 1.25 g of a 10% poly(vinyl alcohol), 110,000 mol. wt., 100% hydrolyzed, solution in water, was treated with 10 μl of 12.5% glutaraldehyde followed by 25 μl of 10% $H_3PO_4$. A 50 mg portion of the resultant slurry was placed into a bandage mold and warmed to 60° C. for 15 minutes. The resulting solid, insoluble, elastomeric bandage composite was aged another 15 min at 60° C. The resultant bandage was soaked in 10 ml of distilled water at 25° C. for 20 minutes. This treatment was repeated two more times with fresh distilled water. Thirteen bandages were prepared as described above. The thirteen, well washed bandages were placed in a mixture of 150 mg ciprofloxacin HCl in 40 ml of distilled water, neutralized to pH 7.0 with 450 μl of 1N NaOH (a fine white precipitate formed). After gentle stirring for 24 hrs at 25° C., a clear solution over the bandage device was obtained. At this point HPLC analysis showed 8.8 mg of ciprofloxacin present in the solution. Thus, the thirteen bandages were each estimated to contain 10.9 mg of ciprofloxacin.

One bandage was subjected to hourly extractions with 1 ml portions of 0.9% NaCl at 25° C. and the extracts were analyzed for ciprofloxacin content by HPLC as described in Example 2. The results of this experiment are reported in Table 6. These results showed that less than 11% of the initial charge of ciprofloxacin was released in the first 4 hours, the release of ciprofloxacin over the subsequent 20 hrs was fairly constant between 100 and 195 μg/ml and the pH of the extracts was 7.0.

TABLE 6

| Time, Hr | μg cipro/ml | Time, Hr | μg cipro/ml | Time, Hr | μg cipro/ml |
|---|---|---|---|---|---|
| 1 | 370 | 9 | 190 | 17 | 115 |
| 2 | 300 | 10 | 170 | 18 | 115 |
| 3 | 240 | 11 | 160 | 19 | 100 |
| 4 | 220 | 12 | 140 | 20 | 110 |
| 5 | 220 | 13 | 130 | 21 | 110 |
| 6 | 198 | 14 | 125 | 22 | 115 |
| 7 | 195 | 15 | 125 | 23 | 115 |
| 8 | 170 | 16 | 115 | 24 | 110 |

EXAMPLE 7

A Cryogel Bead Bandage Containing an Acrylamide-Sulfopropyl Bead Salt of Ciprofloxacin and a Comparison of Elution with Distilled Water vs. 0.9% NaCl A solution of 10 mg of ciprofloxacin HCl in 20 ml of distilled water was neutralized to pH 7.0 with 30 μl of 1N NaOH to give a slurry of fine white crystals. To this slurry was added 100 mg of damp SP Trisacryl M (contains sulfopropyl groups in H+ form, 40 to 140μ diameter) SP Trisacryl M is a trademark owned by IBF Biotechnics, for a sulfopropyl derivatized ion exchange resin. After gentle stirring for 16 hrs at 25° C., HPLC analysis showed 0.032 mg of ciprofloxacin present in the solution. Thus the beads were estimated to contain 9.9 mg of ciprofloxacin. The liquid was drained from the beads and 300 mg of 10% solution of poly(vinyl alcohol), 110,000 mol wt., 100% hydrolyzed, in water, was added. A 100 mg portion of this slurry was cast into a cryogel bandage as described in Example 2. This bandage was estimated to contain about 2.5 mg of ciprofloxacin.

This bandage containing the ciprofloxacin/sulfopropyl resin bead salt was subjected to hourly extractions with 1 ml portions of distilled water at 25° C. and the extracts were analyzed for ciprofloxacin content by HPLC as described in Example 2. At hours 10 and 11, 0.9% NaCl was used. The results of this experiment are shown in Table 7. The data in Table 7 showed that the rate of ciprofloxacin elution was greatly accelerated when distilled water was changed to 0.9% NaCl in water.

TABLE 7

| Time, Hr | μg cipro/ml | Time, Hr | μg cipro/ml | Time, Hr | μg cipro/ml |
|---|---|---|---|---|---|
| 1 | 60 | 5 | 50.5 | 9 | 60 |
| 2 | 60 | 6 | 49 | 10 | 330 |
| 3 | 48 | 7 | 55 | 11 | 310 |
| 4 | 47 | 8 | 49.5 | | |

EXAMPLE 8

The Timed Release of Ciprofloxacin by an Ion Exchange Bandage

To a solution of 11 mg of ciprofloxacin HCl in 10 ml of distilled water, neutralized to pH 7.0 with 30 μl of 1N NaOH was added 100 mg of damp CM-Sephadex M, H+ form. CM-Sephadex M is a trademark owned by Pharmacia, Inc. for carboxy methyl derivatized ion exchange resin beads. After gentle stirring for 16 hrs at 25° C., HPLC analysis showed 0.4 mg of ciprofloxacin present in the solution. Thus the beads were estimated to contain 10.6 mg of ciprofloxacin.

The beads were rinsed twice with 10 ml portions of distilled water, and then with a 1 ml portion of distilled water at 25° C. followed one hour later by 1 ml of 0.9% NaCl. The extracts were analyzed for ciprofloxacin content by HPLC as described in Example 2. After 1 hr the distilled water extract contained 88 μg cipro/ml. After 2 hrs, the 0.9% NaCl extract contained 640 μg/ml. The results indicated that the these carboxyl functionalized Sephadex beads functioned as time release carriers for ciprofloxacin.

EXAMPLE 9

Preparation of a Cryogel Bandage Containing Gentamicin

To prepare the bandage, 100 mg of a 10% polyvinyl alcohol (110,000 molecular weight; 100% hydrolyzed) solution in water solution was placed in a stainless steel mold having a cavity 30 mil thick and 18 mm in diameter. The mold and its contents were subjected to four freeze/thaw cycles of −20° C. for 1 hr followed by 25° C., one hour. The bandage was taken from the mold at this point and placed in 2 ml of water containing 200 mg of gentamicin (Sigma Chem. Co.) for 8 hours. At the end of this time, the solution was analyzed for gentamicin and it was found that the bandage had taken up 9 mg gentamicin.

The bandage was then placed in 2 ml 0.9% saline and the eluted gentamicin was determined by HPLC after the method of P. Arella, et al, (J. Chrom. 348, 229–240, 1985), with a Whatman Partisil 50DS-3 column and a mobile phase of 400 ml water with 1.9 g of $KH_2PO_4$, pH adjusted to 7.5 with 40% KOH, 493 ml of acetonitrile, 120 ml methanol. The sample from the bandage (100 μl) was reacted with 1 ml of 0.5% trinitrobenzene sulfonic acid and 1.25 ml of pyridine. The mix was allowed to stand for 15 min at 70° C., cooled and 1 ml of glacial acetic acid was added and the sample was then analyzed. After 0.5 hr, the concentration of gentamicin in the extract was 2 mg/ml. A fresh batch of 0.9% saline was added to the bandage and analysis of the supernatant at the end of 1.0 hr showed that the concentration was 0.03 mg/ml. Similarly, samples analyzed at the end of 2.0 hours showed that no gentamicin was detectable.

EXAMPLE 10

A Cryogel Bandage Containing Silver Sulfadiazine

To 5.0 g of a 10% solution of poly(vinyl alcohol), 110,000 molecular weight, 100% hydrolyzed, in distilled water, was added 0.05 g of silver sulfadiazine. Several minutes of stirring were required to obtain a homogeneous solution.

A 4.0 g portion of this solution was cast between two glass plates separated by a 0.5 mm shim. The glass plates and contents were subjected to six cycles of −21° C., for 20 minutes followed by 20 minutes at 25° C., to give a 0.5 mm thick by 6–10 cm diameter disk. This disk was a white, semi-translucent, flexible, tough, elastomeric, cryogel containing silver sulfadiazine.

EXAMPLE 11

A Cryogel/Resin Bead Bandage wherein the Resin was Imbibed with Gentamicin and then Incorporated into the Bandage A slurry of 2000 mg of wet CM TRISACRYL (a product of IBF Biotechnics) beads were washed with 2N HCl and then with water. A slurry of 2000 mg these beads (40–80μ diameter) in 19 ml of distilled water containing 31.5 mg of gentamicin, free base were gently stirred for 12 hrs at 25° C. Analysis of the gentamicin in the supernatant liquid indicated that there was 15.2 mg of gentamicin per g of wet loaded beads. A 1000 mg portion of these beads were drained free of the aqueous phase and added to 60 mg of glycerol and 600 mg of a 10% poly(vinyl alcohol), 110,000 mol. wt., 100% hydrolyzed, solution in distilled water was added. A 120 mg portion of the resultant slurry was cast into a bandage by a series of 4 freeze/thaw cycles as described in Example 2 to give a white flexible bandage, 15 mm in diameter and 30 mil thick which was estimated to contain 1.1 mg of gentamicin.

This bandage containing the gentamicin/CM TRISACRYL bead was subjected to hourly extractions with 1 ml portions of 0.9% NaCl at 25° C. and the extracts were analyzed for gentamicin content by the method of Example 9. The results are shown in Table 8.

TABLE 8

| Time, Hr | μg gentamicin/ml | Time, Hr | μg gentamicin/ml | Time, Hr | μg gentamicin/ml |
| --- | --- | --- | --- | --- | --- |
| 0.5 | 300 | 5 | 26 | 10 | 28 |
| 1 | 122 | 6 | 26 | 11 | 28 |
| 2 | 30 | 7 | 26 | 12 | 24 |
| 3 | 28 | 8 | 34 | 13 | 16 |
| 4 | 26 | 9 | 30 | 14 | 8 |

EXAMPLE 12

A Cryogel Bandage Containing Bacitracin

To 5.0 g of a 10% solution of poly(vinyl alcohol), 110,000 molecular weight, 100% hydrolyzed, in distilled water was added 0.1 g of bacitracin (50,000 units per gram). Within seconds at 25° C., a clear homogeneous solution was obtained.

A 4.0 g portion of this solution was cast between two glass plates separated by a 1.0 mm shim. the glass plates and contents were subjected to six cycles of −21° C., for 20 minutes followed by 20 minutes at 25° C., to give a 1 mm thick by 6–10 cm diameter disk. This disk was a flexible, tough elastomeric, translucent cryogel containing dissolved bacitracin.

EXAMPLE 13

A Cryogel Bandage Containing Neomycin

To 5.0 g of a 10% solution of poly(vinyl alcohol), 110,000 molecular weight, 100% hydrolyzed, in distilled water was added 0.1 g of neomycin sulfate (90–95% neomycin B with the remainder being neomycin C). Within seconds at 25° C., a clear homogeneous solution was obtained.

A 4.0 g portion of this solution was cast between two glass plates separated by a 1.0 mm shim. The glass plates and contents were subjected to six cycles of −21° C., for 20 minutes followed by 20 minutes at 25° C., to give a 1 mm thick by 6–10 cm diameter disk. This disk was a flexible, tough elastomeric, translucent cryogel containing dissolved neomycin.

EXAMPLE 14

A Cryogel Bandage Containing Ciprofloxacin HCl

To 1.0 g of a 10% solution of poly(vinyl alcohol), 110,000 molecular weight, 100% hydrolyzed, in distilled water was added 150 mg of ciprofloxacin HCl. After warming this mixture to 60°–65° C., a clear homogeneous solution was obtained.

A 100 mg portion of this solution was cast into a 15 mm diameter×0.375 mm thick disc and subjected to six cycles of −21° C., for 20 minutes followed by 20 minutes at 25° C., to give a 1 mm thick by 6–10 cm diameter disk. This disk was a flexible, tough elastomeric, translucent cryogel containing many minute white clusters of ciprofloxacin HCl crystals.

To demonstrate the release of the ciprofloxacin from the cryogel in a simulated body fluid environment, the cryogel/ciprofloxacin disk was immersed in 1.0 ml portions of 0.9% NaCl in distilled water for 1 hour, after which the procedure was repeated. HPLC analyses of the saline extracts for ciprofloxacin were made. The pH of these saline extracts was found to be 5.5. The initial content of ciprofloxacin in the disk was estimated to be 15 mg. The results are shown in Table 9.

mg of ciprofloxacin HCl in 2 ml of water which had been neutralized to pH 7.0 with 45 μl of 1N NaOH. After 24 hrs at 25° C., HPLC analysis showed essentially all of the ciprofloxacin was no longer in the solu-

TABLE 9

| Time (hr) | ciprofloxacin μg/ml | Time (hr) | ciprofloxacin μg/ml | Time (hr) | ciprofloxacin μg/ml |
|---|---|---|---|---|---|
| 1 | 2680 | 5 | 1400 | 9 | 40 |
| 2 | 2720 | 6 | 680 | 10 | 22 |
| 3 | 2120 | 7 | 360 | | |
| 4 | 1680 | 8 | 260 | | |

EXAMPLE 15

A Cryogel Bandage Containing Ciprofloxacin as a Salt of a Carboxylate Ion Exchange Bead A 100 mg portion of a 50/50 slurry of wet CM SEPHADEX C-25 beads (a product of Pharmacia, Inc.) in 10% poly(vinyl alcohol), 110,000 mol. wt., 100% hydrolyzed, solution in distilled water was cast into a bandage by a series of 6 freeze/thaw cycles as described in Example 14 to give a tough, elastomeric, translucent bandage, 15 mm in diameter and 0.37 mm thick, which was then placed in a solution of 15 mg of ciprofloxacin HCl in 2 ml of water which had been neutralized to pH 7.0 with 45 μl of 1N NaOH. After 24 hrs at 25° C., HPLC analysis showed essentially all of the ciprofloxacin was no longer in the solution. The disk was estimated to contain 15 mg of ciprofloxacin.

This bandage containing the ciprofloxacin/CM SEPHADEX bead was subjected to hourly extractions with 1 ml portions of 0.9% NaCl at 25° C. and the extracts were analyzed for ciprofloxacin content by HPLC. The results are shown in Table 10.

tion. The disk was estimated to contain 15 mg of ciprofloxacin.

This bandage containing the ciprofloxacin/sulfonic acid ion exchange resin beads was subjected to hourly extractions with 1 ml portions of 0.9% NaCl at 25° C. and the extracts were analyzed for ciprofloxacin content by HPLC. The results are shown in Table 11.

TABLE 11

| Time (hr) | ciprofloxacin μg/ml | Time (hr) | ciprofloxacin μg/ml | Time (hr) | ciprofloxacin μg/ml |
|---|---|---|---|---|---|
| 1 | 140 | 9 | 200 | 17 | 120 |
| 2 | 150 | 10 | 240 | 18 | 200 |
| 3 | 180 | 11 | 240 | 19 | 160 |
| 4 | 180 | 12 | 160 | 20 | 200 |
| 5 | 120 | 13 | 120 | 21 | 120 |
| 6 | 140 | 14 | 120 | 22 | 200 |
| 7 | 280 | 15 | 200 | 23 | 120 |
| 8 | 200 | 16 | 200 | 24 | 120 |

EXAMPLE 17

A PVA Cryogel Bandage Containing Resin Beads which was Further Coated to Prevent Loss of the Resin A thick paste was made of 1.0 g styrene sulfonic acid ion exchange resin beads (BioRAd, 35-75 μ diameter), in 0.5 g of 10% poly(vinyl alcohol), 110,000 mol. wt., 100% hydrolyzed, solution in distilled water. This mixture was cast into a 0.375 mm thick membrane and subjected to six cycles of freeze-thaw (−20° to +25° C.) with 20 minutes at each temperature. This bandage was cut into pieces weighing between 40 and 45 mg. Upon gentle shaking of these pieces in water, it was noticed that small quantities of particles were released. The pieces were dipped in a 10% solution of the above

TABLE 10

| Time (hr) | ciprofloxacin μg/ml | Time (hr) | ciprofloxacin μg/ml | Time (hr) | ciprofloxacin μg/ml |
|---|---|---|---|---|---|
| 1 | 1240 | 7 | 680 | 13 | 100 |
| 2 | 1320 | 8 | 640 | 14 | 96 |
| 3 | 1280 | 9 | 520 | 15 | 48 |
| 4 | 1200 | 10 | 360 | 16 | 30 |
| 5 | 1120 | 11 | 200 | | |
| 6 | 1000 | 12 | 120 | | |

EXAMPLE 16

A Cryogel Bandage Containing Ciprofloxacin as a Salt of a Sulfonic Acid Ion Exchange Bead A 100 mg portion of a 50/50 slurry of wet sulfonic acid ion exchange resin beads (a product of BioRad, 35-75μ diameter) in 10% poly(vinyl alcohol), 110,000 mol. wt., 100% hydrolyzed, solution in distilled water was cast into a bandage by a series of 6 freeze/thaw cycles as described in Example 14 to give a tough, elastomeric, translucent bandage, 15 mm in diameter and 0.37 mm thick, which was then placed in a solution of 15 mentioned PVA. After momentarily allowing the coated pieces to drain off the excess PVA solution, the lightly coated objects were subjected to six cycles of freeze-thaw (−20° to +25° C.) with 20 minutes at each temperature. The resultant cured cryogel coated pieces did not exhibit any shedding of solid particles.

Four of the cryogel bandage pieces, estimated to contain a total of 105.6 mg of sulfonic acid resin beads were placed in distilled water containing 50 mg ciprofloxacin in its free base form. Most of the ciprofloxacin free base remained as undissolved particles initially, however, after gently stirring overnight (20 hr) at 25° C., no particles of ciprofloxacin remained. Analysis of the aqueous phase by HPLC showed that it contained only 5.1 mg of dissolved ciprofloxacin or 4.8% while the remaining 95.2% of the ciprofloxacin had been taken up by the bandage pieces.

EXAMPLE 18

A PVA Cryogel/Fabric Composite Bandage

Approximately 30 g of a 10% solution of poly(vinyl alcohol), 110,000 molecular weight, 100% hydrolyzed, in distilled water was poured over a 3"×5" section of two ply cheese cloth. This composition was then sandwiched between glass plates separated by 1 mm thick shims. This was subjected to six cycles of freeze-thaw (−20° to +25° C.) with 30 minutes at each temperature. A flexible solid PVA cryogel-fabric composite was obtained which, although not as elastomeric as similar unfilled PVA cryogel sheets, was much more resistant to tearing.

EXAMPLE 19

A Cryogel Bandage Containing Norfloxacin HCl

To 2.5 g of a 10% solution of poly(vinyl alcohol), 124,000–186,000 molecular weight, 99% hydrolyzed, in distilled water was added 250 mg of norfloxacin HCl. A cloudy homogeneous solution was obtained.

This mixture was cast between two glass plates separated by 0.375 mm shims and subjected to six cycles of −20° C., for one hour followed by one hour at 25° C., to give a flexible, elastomeric, white cryogel membrane containing norfloxacin HCl crystals.

EXAMPLE 20

A Cryogel Resin/Bandage Containing Norfloxacin HCl

To 0.66 g of a 10% solution of poly(vinyl alcohol), 124,000–186,000 molecular weight, 99% hydrolyzed, in distilled water was added 1.0 g of wet CM-SEPHADEX C-25 beads (a product of Pharmacia, Inc., Piscataway, N.J.) in their free carboxylic acid form.

This mixture was cast between two glass plates separated by 0.375 mm shims and subjected to six cycles of −21° C., for one hour followed by one hour at 25° C., to give a flexible, elastomeric, white cryogel membrane containing the ion exchange resin. The membrane was cut into ten 15 mm diameter disks, each weighing about 90 mg. One of the disks was added to a slurry of 15 mg of norfloxacin in 2 ml of distilled water. After 6 hr of gentle stirring at 25° C., all of the solid norfloxacin particles had been taken up by the cryogel/resin disk.

EXAMPLE 21

A Cryogel Bandage Containing Penicillin G and Streptomycin

To 13.5 g of a 10% solution of poly(vinyl alcohol), 124,000–186,000 molecular weight, 99% hydrolyzed, in distilled water was added 1.5 g of Combiotic Suspension (Pfizer Ag. Division, containing 400,000 units of procaine penicillin G and 0.5 g dihydrostreptomycin base+2% procaine-HCl, 2% sodium phosphate, 1.26% sodium citrate, 0.5% povidone, 0.37% sodium formaldehyde sulfoxylate, 0.25% lecithin, 0.2% urea, 0.015% butylparaban, 0.25% phenol), which upon stirring gave a cloudy homogeneous solution.

This mixture was cast between two glass plates separated by 1 mm shims and subjected to six cycles of −20° C., for one hour followed by one hour at 25° C., to give a flexible, elastomeric, white cryogel membrane.

EXAMPLE 22

A Cryogel Bandage Containing Ketoprofen

To 3.0 g of a 10% solution of poly(vinyl alcohol), 124,000–186,000 molecular weight, 99% hydrolyzed, in distilled water was added 0.3 g of ketoprofen, which upon stirring gave a cloudy homogeneous solution.

This mixture was cast between two glass plates separated by 0.375 mm shims and subjected to six cycles of −20° C., for one hour followed by one hour at 25° C., to give a flexible, elastomeric, white cryogel membrane.

EXAMPLE 23

A Cryogel Bandage Containing Gramicidin, Polymyxin B and Neomycin

To 5.0 g of a 10% solution of poly(vinyl alcohol), 124,000–186,000 molecular weight, 99% hydrolyzed, in distilled water was added 2.8 mg of neomycin sulfate, 8.0 mg of polymyxin B and 0.2 mg of gramicidin D, which upon stirring gave a clear homogeneous solution. A 4 g portion of this solution was cast between two glass plates separated by 0.375 mm shims and subjected to six cycles of −20° C., for one hour followed by one hour at 25° C., to give a flexible, elastomeric, white cryogel membrane.

EXAMPLE 24

A Cryogel Bandage Containing Bacitracin, Polymyxin B and Neomycin

To 5.0 g of a 10% solution of poly(vinyl alcohol), 124,000–186,000 molecular weight, 99% hydrolyzed, in distilled water was added 2.8 mg of neomycin sulfate, 8.0 mg of polymyxin B and 6.5 mg of bacitracin, which upon stirring gave a clear homogeneous solution. A 4 g portion of this solution was cast between two glass plates separated by 0.375 mm shims and subjected to six cycles of −20° C., for one hour followed by one hour at 25° C., to give a flexible, elastomeric, white cryogel membrane.

EXAMPLE 25

A Cryogel Bandage Having a Support and a Plasticizer

A mixture of 10 g of poly(vinyl alcohol), 124,000–186,000 molecular weight, 99% hydrolyzed, in 45 g distilled water and 45 g glycerol was heated to 95° C. for two hours with vigorous stirring. A 15 g portion of this solution was poured over and into an 8×15 cm section of Curity Stretch Gauze (A product of Kendall-Futuro Corp) and then sandwiched between glass plates and subjected to one cycle of −20° C., for 30 min followed by standing at 25° C. overnight. There was obtained a sheet of flexible PVA cryogel-cloth composite which was very strong and elastomeric.

EXAMPLE 26

A Cryogel Bandage Having a Plasticizer

A mixture of 10 g of poly(vinyl alcohol), 124,000–186,000 molecular weight, 99% hydrolyzed, in 45 g distilled water and 45 g glycerol was heated to 95° C. for two hours with vigorous stirring. A 18 g portion was cast between two glass plates separated by 1 mm shims and subjected to one cycle of −20° C., for 30 min followed by standing at 25° C. overnight. There was obtained a sheet of flexible, tough PVA cryogel membrane which was very strong and elastomeric and 3.2 g of clear liquid (17.8% syneresis).

EXAMPLE 26A

A Cryogel Bandage Having a Plasticizer and Containing Silver Sulfadiazine

A mixture of 10 g of poly(vinyl alcohol), 124,000–186,000 molecular weight, 99% hydrolyzed, in 45 g distilled water and 45 g glycerol was heated to 95° C. for two hours with vigorous stirring. A 10 g portion was mixed with continuous stirring at 80°–90° C. with 0.11 g silver sulfadiazine micronized powder. Approximately 5 g of the resultant milky white slurry was cast between two glass plates separated by 0.375 mm shims and subjected to one cycle of −20° C., for 30 min followed by standing at 25° C. overnight. There was obtained a sheet of white, flexible, tough PVA cryogel membrane which was very strong and elastomeric and a small amount of clear liquid.

Without plasticization the PVA cryogels become shrunken, hard, leather like solids upon drying. Certain liquid polyols, such as glycerol, glycols, etc., keep the PVA flexible and more elastomeric in the absence of water.

EXAMPLE 26B

PVA Cryogel Containing Glycerol

In all the following formulations, involving glycerol, it was observed that the initial slurries of poly(vinyl alcohol), 124,000–186,000 molecular weight, 99% hydrolyzed, upon stirring at 90° to 100° C. for 1 to 2 hrs became colorless, clear, homogeneous, viscous solutions.

| Components | Properties |
|---|---|
| 1. glycerol, 45 g; water, 45 g; PVA, 10 g | The clear solution at 90° C. becomes a tough translucent, elastomeric solid upon standing several hrs at 25° C. |
| 2. glycerol, 40 g; water, 50 g; PVA, 10 g | The clear solution at 90° C. remains a clear fluid at 25° C. |
| 3. glycerol, 30 g; water, 60 g; PVA, 10 g | Same as 2. |
| 4. glycerol, 20 g; water, 70 g; PVA, 10 g | Same as 2. |

Three gram portions of the four formulations given above were cast between glass plates separated by 0.5 mm shims and cured by three freeze/thaw cycles at −20° C. for one hr and then 1 hr at 25° C., to give clear, flexible elastomers with various degrees of fluid exudation (syneresis). Sections of these elastomers were then allowed to dry for 24 hrs at 25° C. to observe whether the membranes remained flexible. The results are shown in Table 12.

TABLE 12

| Formulation | % syneresis | Wet Dimensions (cm) | Wet Weight (g) | Dry Dimensions (cm) | Dry Weight (g) | Observations (linear shrinkage) |
|---|---|---|---|---|---|---|
| 1. | 43% | 7.3 × 2.6 | 1.1 | 5.98 × 2.2 | 0.5 | 16–19% |
| 2. | 29% | 6.2 × 2.5 | 1.15 | 5.5 × 1.8 | 0.7 | 26–15% |
| 3. | 22% | 7.5 × 2.6 | 1.1 | 5.8 × 2.0 | 0.48 | 23% |
| 4. | 15% | 6.5 × 2.5 | 1.05 | 4.5 × 1.7 | 0.375 | 31% |

All membranes continued to exude liquid while wet and all were flexible when dry with formulation 1 being the most flexible and 4 being the least flexible. The dry membranes had a slightly oily feel.

EXAMPLE 27

PVA Cryogel Containing 1,2-Propanediol

In all the following formulations, involving propylene glycol (PG), it was observed that the initial slurries of poly(vinyl alcohol), 124,000–186,000 molecular weight, 99% hydrolyzed, upon stirring at 90° to 100° C. for 1 to 2 hrs became colorless, clear, homogeneous, viscous solutions.

| Components | Properties |
|---|---|
| 1. PG, 45 g; water, 45 g; PVA, 10 g | The clear solution at 90° C. became slightly more viscous upon standing several hrs at 25° C. |
| 2. PG, 40 g; water, 50 g; PVA, 10 g | Same as 1. |
| 3. PG, 30 g; water, 60 g; PVA, 10 g | Same as 1. |
| 4. PG, 20 g; water, 70 g; PVA, 10 g | Same as 1. |

Three gram portions of the four formulations given above were cast between glass plates separated by 0.5 mm shims and cured by three freeze/thaw cycles at −20° C. for one hr and then 1 hr at 25° C., to give clear, flexible elastomers with various degrees of fluid exudation (syneresis). Sections of these elastomers were then allowed to dry for 24 hrs at 25° C. to observe whether the membranes remained flexible. The results are shown in Table 13.

TABLE 13

| Formulation | % syneresis | Wet Dimensions (cm) | Wet Weight (g) | Dry Dimensions (cm) | Dry Weight (g) | Observations (linear shrinkage) |
|---|---|---|---|---|---|---|
| 1. | 10% | 8.2 × 2.5 | 1.02 | 6.2 × 2.0 | 0.48 | 20% |
| 2. | 7% | 7.5 × 2.3 | .97 | 5.8 × 1.4 | 0.252 | 30% |
| 3. | <1% | 6.2 × 2.4 | .75 | 4.5 × 1.7 | 0.30 | 28% |
| 4. | <1% | 6.4 × 2.4 | .70 | 5.3 × 2.0 | 0.162 | 17% |

All membranes except formulation 4 continued to exude liquid while wet and all were flexible when dry with formulation 1 being the most flexible and 4 being the least flexible. The dry membranes had a slightly oily feel.

EXAMPLE 28

PVA Cryogel Containing 30% 1,2-Propanediol and 1% Silver Sulfadiazine

To 30 g of 1,2-propanediol was added 1.0 g of micronized silver sulfadiazine powder. After several minutes of stirring at 25° C., it was observed that the powder had completely and uniformly dispersed with no evidence of any clumps of solids remaining. The resultant milk white dispersion was easily dispersed in 60 ml of distilled water. To the resultant homogeneous slurry was added 10 g of poly(vinyl alcohol), 124,000–186,000 molecular weight, 99% hydrolyzed. After stirring at 90° to 100° for 1 hr, the PVA dissolved leaving a slightly viscous milky white fluid. Upon standing 48 hrs this fluid became very viscous, with no evidence of any settling of the solids, but it did not solidify.

Several three gram portions of this dispersion were cast between glass plates separated by 0.5 mm shims and cured by three freeze/thaw cycles at −20° C. for one hr and then 1 hr at 25° C., to give white, flexible elastomers with low degrees of fluid exudation (syneresis). One of these, an 8.2 cm diameter ×0.5 cm thick, piece, was placed on the skin of the inner forearm of a human volunteer and covered with a 4"×5" piece of 4 mil thick polyethylene film. The film was held in place with tape around the edges. The whole was then wrapped with a stretch bandage. After 12 hrs, the membrane was recovered essentially unchanged. The soft moist skin beneath the membrane was scraped with a sharp knife to remove 0.2 g of skin. This sample was dispersed in 8.0 ml of a 56% aqueous methanol buffer (0.71 g $K_2HPO_4$/2 L distilled water, pH 7.2 with $H_3PO_4$) and brought to a boil momentarily. After 10 min of additional stirring, the dispersion was filtered through a 0.2μ filter. HPLC analysis (C-18 column, 0.75 ml/min of the above described methanol/water buffer, 354 nm detector, sulfadiazine peak at 4 min) of this filtrate showed that it contained a total of 104 μg of sulfadiazine.

EXAMPLE 29

A Cryogel Coated Ion Exchange Resin which Is Imbibed with a Protein

A 2 g portion of wet Amberlyst A-21 beads (a product of Rohm and Haas) was mixed with 1 g of 10% poly(vinyl alcohol), 124,000–186,000 mol. wt., 99% hydrolyzed, solution in distilled water, and cast into a bandage by a series of 3 freeze/thaw cycles as described in Example 14 to give a tough, elastomeric, translucent bandage from which disks 15 mm in diameter and 0.5 mm thick were cut and then washed three times with 5 mls of 0.005M phosphate buffer, pH 8.2. To each of two discs, similarly prepared, one ml of a solution of 10 mg/ml of bovine serum albumin (BSA) was added and the disk was allowed to imbibe the BSA for 18 hours. The supernatant was assayed by taking a 750 μl sample of the BSA solution and adding 250 μl of a 1 mg/ml fluorescamine in acetone solution, diluting with 3 ml of the above mentioned phosphate buffer and reading the fluorescence using a mercury lamp and Corning 7-39 filter for excitation and a Corning 3-72A filter for emission. The values obtained were compared to a standard curve prepared using appropriate dilutions of known weights of BSA. It was determined that 1.84 mg was bound to disk A and 1.64 to disk B. The discs were washed 3 times with 5 mls of the above mentioned buffer and the last wash contained less than 0.02 mg of BSA.

To determine the release of the protein, one ml of 0.05M phosphate buffer, pH 7.2, containing 0.15% saline was added to the disk and the whole was gently stirred for one hour. The solution was removed and assayed and an additional portion was added and the procedure repeated at 2, 3, 4 and 48 hours. Disk A released 0.11 mg at 1 hr; 0.11 mg at 2 hr; 0.09 mg at 3 hr; 0.06 mg at 4 hr; and 0.23 mg at 48 hr. Disk B released 0.13 mg at 1 hr; 0.14 mg at 2 hr; 0.12 mg at 3 hr; 0.07 mg at 4 hr; and 0.34 mg at 48 hr.

EXAMPLE 30

A Cryogel Coated Ion Exchange Resin which Has Been Imbibed with Ketoprofen

A strong base ion exchange resin (1 g of Biorad AGMP1, 35–75μ diameter bead, 4.2 meq/g) was placed in a solution of 5 g of methanol, 4 g of water and 200 mg of ketoprofen and stirred for 16 hours at 25° C. The beads were separated from the solution and upon HPLC analysis, it was found that 19 mg of ketoprofen remained in the liquid phase. By difference, 181 mg were taken up by the ion exchange resin at the rate of 0.18 mg ketoprofen/mg ion exchange resin.

A 500 mg portion these beads were mixed with 500 mg of 10% poly(vinyl alcohol), 124,000–186,000 mol. wt., 99% hydrolyzed, solution in distilled water and cast into a bandage by a series of 3 freeze/thaw cycles as described in Example 14 to give a tough, elastomeric, translucent membrane. From this membrane were cut a number of 15 mm diameter disks 0.5 mm thick.

One of the disks containing the ketoprofen/ion exchange bead was subjected to hourly extractions with 2 ml portions of 0.1N HCl at 25° C. and the extracts were analyzed for ketoprofen content by HPLC. The results are shown in Table 14.

TABLE 14

| Time (hr) | ketoprofen μg/ml | Time (hr) | ketoprofen μg/ml | Time (hr) | ketoprofen μg/ml |
|---|---|---|---|---|---|
| 1 | 640 | 7 | 220 | 13 | 180 |
| 2 | 240 | 8 | 212 | 14 | 188 |
| 3 | 240 | 9 | 212 | 15 | 180 |
| 4 | 228 | 10 | 208 | 16 | 168 |
| 5 | 220 | 11 | 200 | 17 | 180 |
| 6 | 228 | 12 | 188 | 18 | 140 |
|   |   |   |   | 19 | 148 |
|   |   |   |   | 20 | 132 |

A total of 4140 μg of ketoprofen (76%) was extracted.

It will be apparent to those skilled in the art that the examples and embodiments described herein are by way of illustration and not of limitation, and that other examples may be utilized without departing from the spirit and scope of the present invention, as set forth in the appended claims.

We claim:

1. A cryogel bandage for administering therapeutic agents to sites of trauma in mammals in need of such treatment by administering therapeutic agents thereto, the cryogel bandage comprising over 80% water, poly(vinyl alcohol) polymer, 90-100% hydrolysis, of molecular weight 50,000-250,000 daltons, a therapeutic agent, and insoluble particles capable of adsorbing or forming salts with the therapeutic agent.

2. The bandage of claim 1 further comprising an additive selected from the group of additives consisting of lubricants, pH buffers, plasticizers, and preservatives.

3. The bandage of claim 1 further comprising a support selected from the group of supports consisting of woven fabrics of naturally occurring fibers, woven fabrics of man made fibers, non-woven fabrics of naturally occurring fibers, non-woven fabrics of man-made fibers, strands of naturally occurring fibers, strands of man-made fibers, interconnected strands of man-made fibers and interconnected strands of naturally occurring fibers, polymer foams, and naturally occurring sponges.

4. The bandage of claim 1 wherein the use of said bandage is for the transdermal delivery of drugs to mammals.

5. The bandage of claim 1 wherein the therapeutic agent is selected from the group consisting of the therapeutic agents consisting of bacampicillin, bacitracin, cephalosporins (including cephalothin, cefazolin, cephapirin, cephradine, cephalexin, cefadroxil, cefaclor, cefamandole cefuroxime, cefonicid, ceforanide, cefoxitin, cefotaxime, ceftizoxime, cefoperazone, ceftazidime, ceftriaxone, moxalactam, imipenem/cilastatin), cycloserine, penicillin G, penicillin G benzathine, cloxacillin, dicloxacillin, methicillin, nafcillin, oxacillin, penicillin V, ampicillin, amoxicillin, bacampicillin, syclacillin, carbenicillin, tircarcillin, mezlocillin, piperacillin, azlocillin, amdinocillin, penicillins combined with clavulanic acid), vancomycin, other β-lactam antibiotics, gramicidin, actinomycin D, doxorubicin, mitomycin C, novobiocin, plicamycin, rifampin, bleomycin, amikacin, chloramphenicol, clindamycin, erythromycin, oleandomycin, gentamicin, kanamycin, lincomycin, neomycin, netilmicin, paromomycin, spectinomycin, streptomycin, tetracycline, oxytetracycline, demeclocycline, doxycycline, methacycline, minocycline, tobramycin, troleandomycin, amphotericin B, colistin, nystatin, polymyxin, griseofulvin, nalidixic acid, pipemidic acid, cinoxacin, norfloxacin, ciprofloxacin, pefloxacin, fleroxacin, enoxacin, ofloxacin, tosulfloxacin, lomefloxacin, sulfacetamide, sulfisoxazole diolamine, salts of monovalent and divalent cations, inorganic and organic silver salts, inorganic and organic zinc salts, inorganic and organic cerium salts, cecropionins, mangainins, iodine, povidone iodine, boric acid, sodium borate, oxydale, potassium permanganate, ethanol, isopropanol, formalin, cresol, dimazole, siccanin, phenyliodoundecynoate, hexachlorophene, resorcin, benzethonin chloride, sodium lauryl sulfate, mercuric chloride, meclocycline, mercurochrome, chlorhexidine gluconate, alkylpolyaminoethylglycine hydrochloride, benzalkonium chloride, nitrofurazone, nystatin, acesulfamin, clotrimazole, sulfamethizole, tolnaftate, pentamycin, amphotericin B, pyrrolnitrin, undecylenic acid, miconazole, trichomycin, variotin, haloprogin, and dimazole hydrochloride, idoxuridine, trifluridine, vidarabine, DDCl, acyclovir, gancyclovir, pyrimethamine, trisulfapyrimidine, flucytosine, AZT, fentanyl, cortisone, hydrocortisone, prednisolone, prednisone, dexamethasone, fluocinolone, silver sulfadiazine, fluorinated-corticoids, diclofenac, ibuprofen, naproxen, ketoprofen, S-ketoprofen, aclacinomycin, retinoic acid, methotrexate, doxorubicin, IL-1$\alpha$, IL-2, IL-2$\beta$, IL-3, IL-4, bleomycin, mitomycin, taxol, cis-platinum, bisantrene, CCNU, activated cytoxan, DTIC, HMM, melphalan, mithromycin, procarbazine, VM25, VP16, tamoxifen, plicamycin, 5-fluorouracil, daunorubicin, mitomycin C, tegafur, carmofur, pipobroman, peplomycin, naphazoline, pheniramine, cromolyn, homochlorcyclizine hydrochloride, atenolol, propranolol, bunitrolol, diphenhydramine hydrochloride, chlorpheniramine, dehydrocholic acid, diflunisal, ethacrynic acid, fenoprofen, furosemide, gemfibrozil, phenytoin, probenecid, sulindac, theophylline, salicyclic acid, acetylsalicyclic acid, acetopenazine, amitriptyline, amphetamine, benztropine, biperiden, bromodiphenhydramine, brompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levoproproxyphene, maprotiline, meclizine, mepenzolate, meperidine, mephentermine, mesoridazine, methadone, methdilazine, methscopolamine, methysergide, metoprolol, nortryptiline, noscapine, nylindrin, orphenadrine, papaverine, pentazocine, phendimetrazine, phentermine, phenylpropanolamine, pyrilamine, tripelennamine, triprolidine, promazine, propoxyphene, propanolol, pseudoephedrine, pyrilamine, quinidine, scopolamine, dextromethorphan, aminocaproic acid, aminosalicyclic acid, hydromorphone, isoxsuprine, levorphanol, melphalan, morphine, nalidixic acid, paraaminosalicylic acid, diphenylimidazole, glycyrrhetic acid, tranilast, ketotifen, TPA, urokinase, streptokinase, pro-urokinase, superoxide dismutase, lymphokines, monokines, interferon $\alpha,\beta,\pi$-1b,$\alpha$-n3, $\alpha$-2b,$\alpha$-2b, IL-2, tumor necrosis factor, epithelial growth factor, somatrem, fibronectin, GM-CSF, CSF, platelet derived growth factor, somatotropin, rG-CSF, epidermal growth factor, IGF-1, monoclonal and polyclonal antibodies active against venoms, toxins, tumor necrosis factor, and bacteria, epinephrine, levarterenol, thyroxine, thyroglobulin, oxytocin, vasopressin, ACTH, somatropin, thyrotropin, insulin, parathyrin, calcitonin, cyclosporin, tissue plasminogen activator, streptokinase, pro-urokinase, urokinase, vitamins A, B and its subvitamins, C, D, E, F, G, J, K, N, P, PP, T, U and their subspecies, arginine, histidine, proline, lysine, methionine, alanine, phenylalanine, aspartic acid, glutamic acid, glutamine, threonine, tryptophan, glycine, isoleucine, leucine, Prostaglandin $E_1$, $E_2$, $F_{2\alpha}$, and $I_2$, pepsin, pancreatin, rennin, papain, trypsin, pancrelipase, chymopapain, bromelain, chymotrypsin, streptokinase, urokinase, tissue plasminogen activator, fibrinolysin, desoxyribonuclease, sutilains, collagenase, asparaginase, heparin, nitroglycerin, 1,2,3-propanetriolmononitrate, 1,2,3-propanetriolnitrate and their ester derivatives, isosorbide dinitrate, isosorbide-5-mononitrate, pentaerythritol tetranitrate, papaverine hydrochloride, hepronicate, molsidomine, nicomol, simfibrate, diltiazem hydrochloride, cinnarizine, dipyridamole, trapidil, trimetazidine hydrochloride, carbocromene, prenylamine lactate, dilazep dihydrochloride, pindolol, disopyramide, bupranolol hydrochloride, trichlormethiazide, furosemide, prazosin hydrochloride, metoprolol tartrate, carteolol hydrochloride, oxprenolol hydrochloride, propanolol hydrochloride, metildigoxin, caffeine, dopamine hydrochloride, dobutamine hydrochloride, octopamine hydrochloride, diprophylline, ubidecarenon, digitalis, digoxin, clonidine, nifedipine, nicardipine, verapamil, lidocaine, benzocaine, ethyl aminobenzoate, procaine hydrochloride, dibucaine, procaine, mefruside, penflutizide, bumetamide, hydrothiazide, bentroflumethiazide, reserpine, methaqualone, glutethimide, flurazepam, bromovalerylurea, flurazepam hydrochloride, haloxazolam, traizolam, phenobarbital, chloral hydrate, nimetazepam, estazolam, levodopa, fluphenazine, flutazolam, phenobarbital, methylphenobarbital, thioridazine, diazepam, benzbromarone, clocapramine hydrochloride, clotiazepam, chlorpromazine, haloperidol, lithium carbonate, sulfadimethoxine, sulfisoxazole, sulfisomidine, ethambutor hydrochloride, isoniazide, calcium paraaminosalicylate, nicardipine hydrochloride, cinepazide maleate, pentoxifylline, ifenprodil tartrate, aceglutamide aluminum, cetraxate hydrochloride, pirenzepine hydrochloride, cimetidine, L-glutamine, gefarnate, and any stereoisomer of any of these compounds, and the pharmaceutically acceptable salts of these compounds, such compound used singly or in combination of more than one compound, properly chosen.

6. The bandage of claim 1 wherein the insoluble particles capable of adsorbing or forming salts with the therapeutic agent are an ion exchange beads functionalized with a acid.

7. The bandage of claim 1 wherein the insoluble particles capable of adsorbing or forming salts with the therapeutic agent are an ion exchange beads functionalized with a base.

8. The bandage of claim 1 wherein the insoluble particles capable of adsorbing or forming salts with the therapeutic agent are a hydrophobic resin particles.

* * * * *